(12) United States Patent
Collins et al.

(10) Patent No.: US 10,453,182 B2
(45) Date of Patent: Oct. 22, 2019

(54) MEDICAL IMAGING RECONSTRUCTION OPTIMIZED FOR RECIPIENT

(71) Applicant: KONINKLIJKE PHILIPS N.V., Eindhoven (NL)

(72) Inventors: John Patrick Collins, Cleveland Heights, OH (US); Chi-Hua Tung, Aurora, OH (US); Bin Zhang, Cleveland, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 13 days.

(21) Appl. No.: 14/363,917

(22) PCT Filed: Dec. 12, 2012

(86) PCT No.: PCT/IB2012/057213
§ 371 (c)(1),
(2) Date: Jun. 9, 2014

(87) PCT Pub. No.: WO2013/088353
PCT Pub. Date: Jun. 20, 2013

(65) Prior Publication Data
US 2014/0369577 A1  Dec. 18, 2014

Related U.S. Application Data

(60) Provisional application No. 61/576,063, filed on Dec. 15, 2011.

(51) Int. Cl.
*G06T 5/00* (2006.01)
*G06F 16/583* (2019.01)
(Continued)

(52) U.S. Cl.
CPC .............. *G06T 5/00* (2013.01); *A61B 6/5205* (2013.01); *A61B 6/5294* (2013.01); *A61B 6/563* (2013.01);
(Continued)

(58) Field of Classification Search
CPC ......... G06F 16/583; G16H 30/20; G06T 5/00; G06T 7/0012; G06T 11/005;
(Continued)

(56) References Cited

U.S. PATENT DOCUMENTS 5,454,019 A    9/1995  Migita et al.
5,818,896 A *  10/1998 Hsieh .................... A61B 6/032
                                                    378/15
(Continued)

FOREIGN PATENT DOCUMENTS

JP    H08238223     9/1996
JP    2007325641   12/2007

OTHER PUBLICATIONS

Xu et al. "High performance tomosynthesis enabled via a GPU-based iterative reconstruction framework." Medical Imaging 2009: Physics of Medical Imaging. vol. 7258. International Society for Optics and Photonics, 2009.*

(Continued)

*Primary Examiner* — Katrina R Fujita (57) ABSTRACT

A database (52) stores image recipient reconstruction profiles each comprising image reconstruction parameter values. An image reconstruction module (30) is configured to reconstruct medical imaging data to generate a reconstructed image. An image reconstruction setup module (50) is configured to retrieve an image recipient reconstruction profile from the database (52) for an intended image recipient associated with a set of medical imaging data and to invoke the image reconstruction module (30) to reconstruct the set (Continued)

of medical imaging data using image reconstruction parameter values of the retrieved image recipient reconstruction profile to generate a reconstructed image for the intended image recipient. A feedback acquisition module (54) is configured to acquire feedback from the intended image recipient pertaining to the reconstructed image for the intended image recipient. A profile updating module (56) is configured to update the image recipient reconstruction profile of the intended image recipient based on the acquired feedback.

20 Claims, 3 Drawing Sheets

(51) Int. Cl.
*G06T 7/00* (2017.01)
*A61B 6/00* (2006.01)
*G06T 11/00* (2006.01)
*G16H 30/20* (2018.01)
*A61B 6/03* (2006.01)

(52) U.S. Cl.
CPC .......... *G06F 16/583* (2019.01); *G06T 7/0012* (2013.01); *G06T 11/005* (2013.01); *G16H 30/20* (2018.01); *A61B 6/032* (2013.01); *A61B 6/037* (2013.01); *G06T 2207/30004* (2013.01)

(58) Field of Classification Search
CPC .......... G06T 2207/30004; A61B 6/032; A61B 6/037; A61B 6/5205; A61B 6/5294; A61B 6/563
See application file for complete search history.

(56) References Cited

U.S. PATENT DOCUMENTS

| | | | |
|---|---|---|---|
| 6,208,762 B1* | 3/2001 | Garland et al. | 382/254 |
| 6,260,021 B1 | 7/2001 | Wong et al. | |
| 6,411,836 B1 | 6/2002 | Patel et al. | |
| 6,526,304 B1* | 2/2003 | Patel | G06F 19/321 128/920 |
| 6,529,575 B1 | 3/2003 | Hsieh | |
| 6,529,757 B1* | 3/2003 | Patel | G06F 19/321 128/920 |
| 7,376,255 B2 | 5/2008 | De Man et al. | |
| 7,386,088 B2 | 6/2008 | Deman et al. | |
| 7,525,526 B2* | 4/2009 | Brown Elliott | G06T 3/4007 345/100 |
| 7,697,743 B2* | 4/2010 | Metz | 382/131 |
| 8,837,794 B2* | 9/2014 | Nakamura | A61B 5/416 382/128 |
| 2004/0008900 A1 | 1/2004 | Jabri | |
| 2004/0064037 A1* | 4/2004 | Smith | G06T 7/0012 600/420 |
| 2004/0109594 A1* | 6/2004 | Luo | G06T 7/11 382/132 |
| 2004/0122790 A1* | 6/2004 | Walker | G06F 19/321 |
| 2005/0110748 A1 | 5/2005 | Boeing et al. | |
| 2006/0017986 A1* | 1/2006 | Schmidt | G06F 19/321 358/448 |
| 2006/0274145 A1* | 12/2006 | Reiner | G06F 17/3028 348/62 |
| 2007/0071294 A1* | 3/2007 | Mahesh | G06F 19/321 382/128 |
| 2008/0175460 A1* | 7/2008 | Reiner | G06F 17/30244 382/131 |
| 2008/0240533 A1 | 10/2008 | Piron | |
| 2009/0003679 A1* | 1/2009 | Ni | A61B 6/025 382/132 |
| 2009/0169073 A1 | 7/2009 | Areste et al. | |
| 2009/0290773 A1 | 11/2009 | Holt | |
| 2010/0054556 A1* | 3/2010 | Novatzky | G06F 19/321 382/128 |
| 2010/0119136 A1* | 5/2010 | Itagaki | A61B 5/055 382/131 |
| 2010/0145182 A1* | 6/2010 | Schmidt | G06Q 50/22 600/410 |
| 2010/0215140 A1 | 8/2010 | Sauer et al. | |
| 2013/0129165 A1* | 5/2013 | Dekel | G06F 19/321 382/128 |

OTHER PUBLICATIONS

Image Correlation; 1999; Comprehensive Dictionary of Electrical Engineering; CRC Press-IEEE Press; p. 320.

\* cited by examiner

MEDICAL IMAGING RECONSTRUCTION OPTIMIZED FOR RECIPIENT

The following relates to the medical arts, medical imaging arts, imaging-based medical diagnosis and treatment arts, medical image reconstruction arts, and related arts.

Medical imaging is an important tool in clinical assessment, diagnosis, and monitoring, and is used in diverse applications such as tumor assessment, radiation therapy planning and monitoring, cardiac assessment, and so forth. A medical imaging system is a specialized device. In most medical facilities (e.g., hospitals, clinics, or so forth) medical imaging is performed as follows. First, a doctor, radiologist, or other medical professional (hereinafter "physician") examines the patient and orders a medical imaging session. The patient is transferred to a medical imaging facility, which may be in the hospital, or may be an external contracting or affiliated facility. At the medical imaging facility, a technologist performs imaging data acquisition as per the physician's order, and reconstructs the imaging data to generate human-viewable images. The technologist is knowledgeable about the medical imaging system and the capabilities of the ancillary image reconstruction, but is not necessarily a medical doctor and is usually not trained or authorized to promulgate medical conclusions based on the reconstructed medical images. Rather, the reconstructed medical images are sent back to the physician, either as physical printouts, or as data files sent via email, or as data files stored in a Picture Archiving and Communications System (PACS) to be retrieved by the physician, or so forth. The physician then reviews the images, draws medical conclusions from the images, and optionally initiates or updates patient treatment based on those conclusions.

The medical imaging facility may house more than one imaging system of a given imaging modality. These imaging systems may include different models from the same manufacturer, and/or models from different manufacturers. Moreover, a given imaging system has a finite operational life after which it is replaced by a (typically newer) imaging system. These various imaging systems may produce images with different characteristics (e.g., resolution, dynamic range, or so forth) using different default parameters (e.g., different default filters and filter settings). The medical imaging facility may be staffed by two, three, four, or more (perhaps many more) technologists with various levels of training, background, imaging experiences, and so forth. These various technologists may have different opinions as to the "best" set of parameters to use for a given image reconstruction, and thus different technologists may produce images with different types of "tuning".

All of this is transparent to the physican. From the physician's vantage, medical imaging operates as follows: (1) write up an order for a medical image and (2) receive the ordered medical image. If the physician is unhappy with the quality of the received medical image, he or she may request that the image reconstruction be repeated with different parameters. This takes valuable time, both in terms of computer processing and in terms of technician time to translate the physician's request into adjustments in the reconstruction parameters. It may also not be clear what aspect of the reconstruction needs to be modified in order to satisfy the physician.

Further, the modified reconstruction setup preferred by the physician is not generally stored. In some cases the technician may remember the physician's preferred reconstruction setup and use it in future studies, but this is not always the case. Also, in a large facility the same technician may not always be performing the image reconstruction for the physician. Still further, if there are multiple reviewers (e.g. a prescribing physician and a specialist), each may have different views on image quality.

These considerations also adversely impact imaging system manufacturers. The manufacturer typically drives for improved image quality using objective parameters. However, the objectively better image may not be the image preferred by the physician, who is the one making a diagnosis and thus needs to be comfortable with the images. It is difficult or impossible for the manufacturer to provide a "one-size-fits-all" reconstruction that will satisfy every physician making use of the imaging system. At present, this is accommodated by individually adjusting the reconstruction based on feedback from the individual physician. The result is mutually exclusive and generally subjective instructions from different physicians having different image reconstruction preferences.

The following contemplates improved apparatuses and methods that overcome the aforementioned limitations and others.

According to one aspect, an apparatus comprises a database storing image recipient reconstruction profiles wherein each image recipient reconstruction profile comprises image reconstruction parameter values, and an electronic processor configured to generate a reconstructed image from medical imaging data by a process including: retrieving an image recipient reconstruction profile from the database for an intended image recipient; and reconstructing the medical imaging data using image reconstruction parameter values of the retrieved image recipient reconstruction profile to generate the reconstructed image. In some embodiments the electronic processor is further configured to perform a profile updating process including: collecting feedback on the reconstructed image from the intended image recipient; and updating the image recipient reconstruction profile for the intended image recipient based on the collected feedback.

According to another aspect, a method comprises: retrieving an image recipient reconstruction profile for an intended image recipient from a database that stores image recipient reconstruction profiles wherein each image recipient reconstruction profile comprises image reconstruction parameter values; and reconstructing the medical imaging data using image reconstruction parameter values of the retrieved image recipient reconstruction profile to generate the reconstructed image. In some embodiments at least the retrieving and the reconstructing are performed by an electronic processor. In some embodiments the method further comprises: collecting feedback on the reconstructed image from the intended image recipient; and updating the image recipient reconstruction profile for the intended image recipient based on the collected feedback; wherein at least the updating is performed by the electronic processor. In some embodiments a non-transitory storage medium stores instructions executable by an electronic processor to perform a method as set forth in this paragraph.

According to another aspect, an apparatus comprises: a database storing image recipient reconstruction profiles wherein each image recipient reconstruction profile comprises image reconstruction parameter values; an image reconstruction module configured to reconstruct medical imaging data to generate a reconstructed image; and an image reconstruction setup module configured to retrieve an image recipient reconstruction profile from the database for an intended image recipient associated with a set of medical imaging data and to invoke the image reconstruction module to reconstruct the set of medical imaging data using image reconstruction parameter values of the retrieved image recipient reconstruction profile to generate a reconstructed image for the intended image recipient. The image reconstruction module and the image reconstruction setup module are suitably implemented by an electronic processor. In some embodiments the apparatus further comprises: a feedback acquisition module configured to acquire feedback from the intended image recipient pertaining to the reconstructed image for the intended image recipient; and a profile updating module configured to update the image recipient reconstruction profile of the intended image recipient based on the acquired feedback. The feedback acquisition module and the profile updating module are also implemented by an electronic processor.

According to another aspect, a method comprises: executing image reconstruction operations using an electronic processor wherein each image reconstruction operation reconstructs imaging data into a reconstructed image for an intended image recipient using reconstruction parameters specific to the intended image recipient; and displaying or printing reconstructed images for the intended image recipients. The method may further include updating the reconstruction parameters specific to respective intended image recipients based on feedback on the reconstructed images received from the respective intended image recipients. In some embodiments the updating of reconstruction parameters specific to an intended image recipient is based on feedback from the intended image recipient comprising an image quality comparison between two or more reconstructed images for the intended image recipient.

One advantage resides in providing images tuned to the preferences of the physician or radiologist for whom the images are intended, and with which tuned images the physician or radiologist is likely to be comfortable.

Another advantage resides in providing images of improved clinical value as ancillary issues such as image sharpness or noise level are mitigated by providing the physician or radiologist with images tuned to the recipient's individual preferences.

Another advantage resides in providing the foregoing advantages without requiring the physician or radiologist to develop an in-depth understanding of medical imaging and the image reconstruction process.

Numerous additional advantages and benefits will become apparent to those of ordinary skill in the art upon reading the following detailed description.

The invention may take form in various components and arrangements of components, and in various process operations and arrangements of process operations. The drawings are only for the purpose of illustrating preferred embodiments and are not to be construed as limiting the invention.

Disclosed herein are imaging systems and methods in which a physician can specify his or her preferred reconstruction parameter values. This enables the reconstruction to be tailored to the preferences of specific physicians, and avoids a "one-size-fits-all" reconstruction. To achieve this, the disclosed approaches use different reconstruction parameter values (i.e., different reconstruction "profiles") for different physicians. Moreover, since it is recognized herein that a typical physician may not be well-versed in the specific reconstruction algorithm and its particular parameters, the disclosed approaches enable the physician to indirectly specify preferred reconstruction parameter values through the intermediary of providing an image quality assessment for one or more reconstructed images. The disclosed approaches use this indirect information to determine the physician's parameter value preferences. In some embodiments, the physician is provided with reconstructed images in which one parameter is varied, and the physician merely comparatively rates the images, e.g. as image "A" is better than image "B". The value of the varied parameter is then adjusted in the physician's reconstruction profile in accord with the value used in generating the image the physician rated as being of best quality. A set of preferred reconstruction settings (i.e., a "physician profile") is stored for each physician so that subsequent image reconstructions are performed in accordance with the preferences of the specific physician to receive the images. If the physician does request that a reconstruction be done using different settings, this information can be used to update the physician's profile so that the profile reflects the current preferences of the physician.

Figure 1:
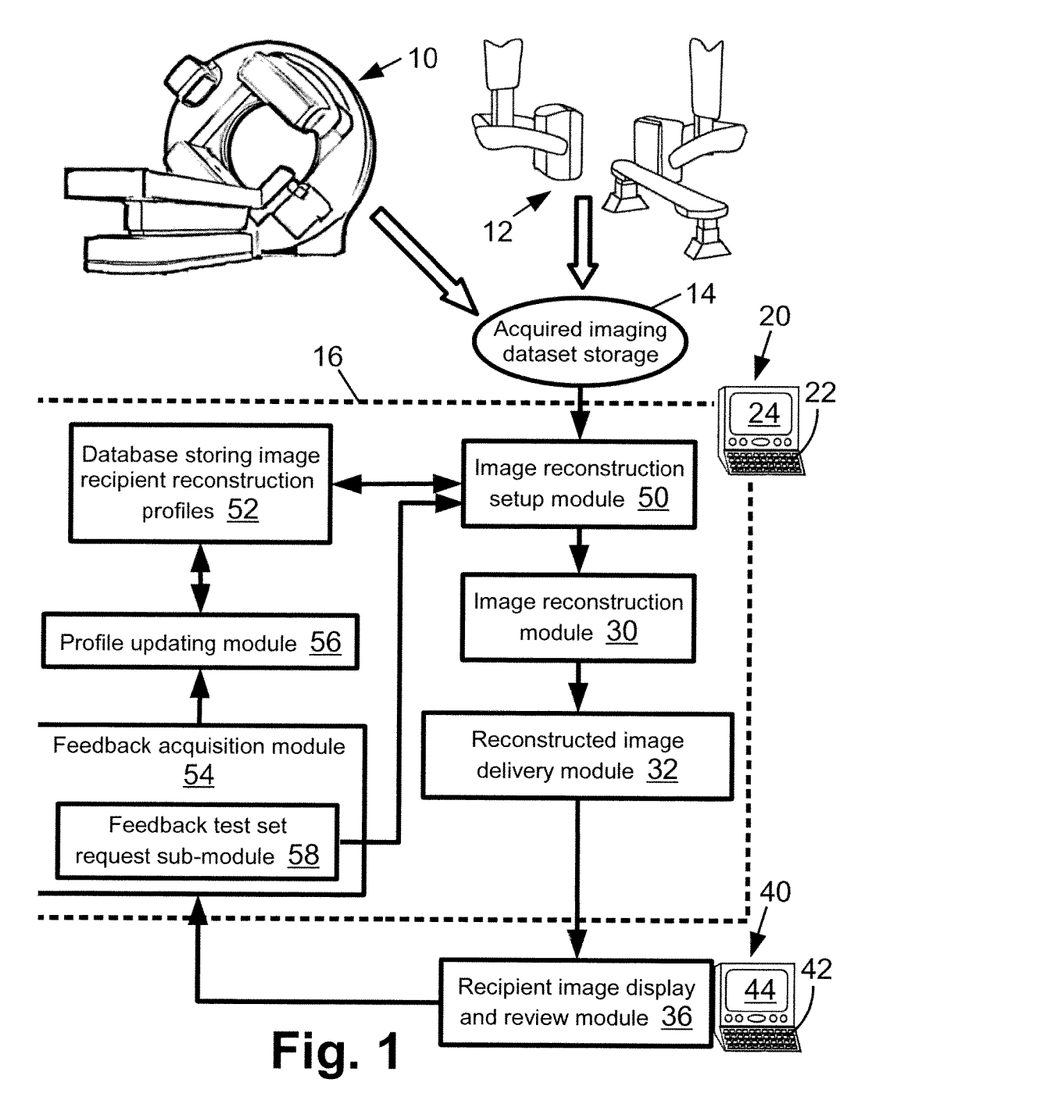
FIG. 1 diagrammatically shows a medical imaging facility and an image display workstation for viewing images generated by the medical imaging facility.

With reference to FIG. 1, some disclosed imaging systems and methods are described. FIG. 1 diagrammatically indicates an imaging facility represented by two imaging apparatuses 10, 12, an acquired imaging dataset storage 14, and an electronic processor 16 configured to reconstruct imaging data to generate a reconstructed image in accordance with approaches disclosed herein. The illustrative imaging apparatuses 10, 12 are both gamma cameras for acquiring radiological imaging data such as single photon emission computed tomography (SPECT) data. The gamma camera 10 employs a rotating gantry supporting robotically manipulated detector heads, while the gamma camera 12 employs detector heads mounted on articulated robotic arms without a gantry. The gamma camera 10 may, for example, be embodied as a BrightView™ SPECT system while the gamma camera 12 may, for example, be embodied as a SKYLight™ nuclear camera (both available from Koninklijke Philips Electronics N.V., Eindhoven, The Netherlands). More generally, the imaging apparatuses 10, 12 can be embodied as imaging apparatuses for acquiring one or more imaging modalities, such as one or more magnetic resonance (MR) scanners, one or more transmission computed tomography (CT) scanners, one or more SPECT imagers (as illustrated), one or more positron emission tomography (PET) scanners, or so forth. In general, the imaging apparatuses 10, 12 may be all from the same manufacturer, or may include imaging systems from different manufacturers. Moreover, the number of imaging apparatuses of the imaging facility can be as few as a single imaging apparatus and has no upper limit. While the two illustrative imaging apparatuses 10, 12 are shown together, it is contemplated for the imaging apparatuses to be located in in different rooms, or even different buildings.

The acquired imaging dataset storage 14 can be embodied as substantially any type of data storage, e.g. magnetic, optical, electronic, or so forth, and may comprise a single data storage device or a plurality of data storage devices (e.g., there may be a separate imaging dataset storage for each imaging system in some embodiments).

The electronic processor 16 is suitably embodied by an illustrative computer 20 having a keyboard 22 or other input device or devices (e.g., a mouse or other pointing device) and a display 24 or other output device or devices (e.g., a printer for generating a hardcopy). In general, the electronic processor 16 can be variously embodied as a desktop computer, notebook computer, network-based server computer, graphical processing unit (GPU), or so forth. In some embodiments the storage 14 is integrated with the electronic processor 16, e.g. as a hard disk drive of the electronic processor.

The electronic processor 16 implements an image reconstruction system. Toward this end, the electronic processor 16 implements an image reconstruction module 30 employing a suitable image reconstruction technique such as iterative forward/backward projection reconstruction, Fourier transform reconstruction, or so forth. The reconstruction module 30 reconstructs an acquired medical imaging data set from the dataset storage 14 to generate a reconstructed image that is distributed by a reconstructed image delivery module 32 to an intended image recipient (for example, a physician, or a radiologist, or so forth). The delivery module 32 may, for example, comprise a Picture Archiving and Communication System (PACS) that stores the reconstructed image and is available at least over a medical data network, and possibly also over the Internet in conjunction with suitable security safeguards (e.g., a secure login accessible only by authorized medical personnel). The delivery module 32 may take other forms, such as an automated electronic mail (email) system that emails the reconstructed image to the intended image recipient at the recipient's email address. It is alternatively contemplated for the functionality of the delivery module 32 to be implemented manually, for example by physically printing out the reconstructed image and manually delivering the printed reconstructed image to the intended image recipient via regular mail, courier, an internal mail system of the medical facility, or so forth.

The intended image recipient receives the reconstructed image, for example as an electronic image, although a physical printout is also contemplated. In the case of an electronic image, the intended image recipient (e.g., physician or radiologist) typically views the image via a recipient image display and review module 36 suitably implemented by a computer or workstation 40 having a keyboard 42 or other input device or devices (e.g., a mouse or other pointing device) and a display 44 or other output device or devices (e.g., a printer for generating a hardcopy). In general, the display/review module 36 can be variously embodied as a desktop computer, notebook computer, a "dumb" terminal in operative communication with a network-based server computer, graphical processing unit (GPU), or so forth. Typically the display 44 is a high resolution graphical color or monochrome display that can provide a high quality display of the reconstructed image, possibly including features such as enlargement or zoom, various false color renderings, image filtering, slice or region extraction (in the case of three-dimensional or volumetric or multi-slice images), cinematic (CINE) sequence display (in the case of images with a time dimension), or so forth. The intended image recipient is typically a physician or radiologist, who makes use of the displayed image to draw medical conclusions or perform other medical operations. The recipient image display and review module 36 is illustrated in FIG. 1 as being implemented by the computer or workstation 40 which is different from the computer 20 that implements the reconstruction system; however, it is also contemplated for the two electronic processors 20, 40 to be embodied as a single computer or other single electronic processor.

In this regard, in some embodiments the display/review module 36 includes therapy planning capability. For example, if the intended image recipient is an oncologist and the reconstructed image is a planning image for use in radiation therapy planning, then the display/review module 36 suitably includes image segmentation capability via which the oncologist can delineate the malignant tumor to be irradiated and neighboring critical organs whose radiation exposure is to be limited. Optionally, the display/review module 36 with image segmentation capability may further include radiation therapy planning capability such as inverse modulated radiation therapy (IMRT) planning is performed to compute multileaf collimator (MLC) settings or other parameter values for performing radiation therapy. As another clinical example, the intended image recipient may be a cardiologist and the reconstructed image is of the heart and surrounding vasculature. In this case the display/review module 36 may include capabilities such as image segmentation (here used to delineate features such as the heart and its constituents such as the atria and ventricles) and analytical tools such as computation of cardiac volume.

As previously discussed, it is recognized herein that different intended image recipients (e.g., different physicians or radiologists) may have different preferences as to the "best" image reconstruction parameter values to employ. For example, one image recipient may prefer a smoother image provided by strong filtering, even at the expense of some loss of fine detail or sharpness due to the strong filtering, or a lower image resolution. On the other hand, another image recipient may prefer the opposite: retention of fine detail and sharpness and maximum image resolution, even at the expense of higher noise or potential artifacts or other so forth. Yet another image recipient, who has spent most of his or her career reading images generated by an older imaging system, may prefer images reconstructed with parameter values that mimic that older system, even if the resulting reconstructed image is objectively not as good as that which is achievable with the newer imaging system (which may, for example, be capable of higher image resolution, higher SNR, or so forth). It is recognized herein that it is advantageous from a medical standpoint to provide the intended image recipient with a reconstructed image having the characteristics preferred by that recipient, even if that reconstructed image would not be preferred by the technologist who operates the electronic processor 16 to perform the image reconstruction.

Toward this end, an image reconstruction setup module 50 implemented by the electronic processor 16 performs reconstruction setup operations. The setup module 50 identifies the imaging data set to be reconstructed and the reconstruction algorithm to employ (if the reconstruction module 30 is capable of employing different reconstruction algorithms). These identification operations may be automated or may utilize identifying input provided by the technologist operating the electronic processor 16 to perform the image reconstruction. Additionally, the setup module 50 accesses a database 52 that stores image recipient reconstruction profiles for the various image recipients served by the imaging facility. Each image recipient reconstruction profile includes image reconstruction parameter values that are preferred by the corresponding image recipient. The parameters whose values are stored in the database 52 may include (but are not limited to): number of iterations (for an iterative reconstruction algorithm such as iterative forward/backward projection reconstruction), pixel or voxel size, relaxation factor, image filter parameters (e.g., filter order, cutoff frequency, et cetera), parameters relating to motion compensation, image truncation, or so forth. Each profile is for a respective image recipient, and contains parameter values that are, in general, different from those of other image recipients. By retrieving the image recipient reconstruction profile from the database 52 for the intended image recipient, and reconstructing the medical imaging data using image reconstruction parameter values of the retrieved image recipient reconstruction profile to generate the reconstructed image, it follows that the reconstructed image is in accordance with the preferences of the intended image recipient.

The image recipient is typically a physician or radiologist who may not be sufficiently knowledgeable about the image reconstruction algorithm to directly specify his or her preferred image reconstruction parameter values. Accordingly, a feedback acquisition module 54 implemented by the electronic processor 16 acquires indirect feedback about image quality preferences from the intended image recipient, and a profile updating module 56 implemented by the electronic processor 16 determines an updated value for a parameter (or updated values for multiple parameters) based on this feedback and updates the profile in the database 52 with the updated parameter value or values.

The feedback acquisition module 54 may be configured to acquire probative feedback in various ways. In a direct assessment approach, the image recipient explicitly rates the image. In one implementation, the display and review module 36 includes a plug-in or other feature providing an image rating dialog window or box. Optionally, the dialog window or box may be user-configurable. In some embodiments the rating is an aggregate rating (for example, a query such as "Please rate the quality of this image on a scale of 0 to 100, where '0' is an unacceptably poor image and '100' is an image of the highest quality" with an integer response bounded to be in the range [0,100]). Alternatively, the image quality rating can be respective to multiple criteria, such as contrast, crispness, or so forth. In this approach the rating feedback for the current reconstructed image is compared with previous ratings by the same image recipient for earlier reconstructed images that employed the same reconstruction algorithm or otherwise are fairly comparable, and the various ratings are correlated with the reconstruction parameter values used in generating the respective reconstructed images. The rating difference between the current reconstructed image and the various earlier images determines the degree of change. This approach can also be used without any comparative images if the ratings pertain to identifiable aspects of image quality. For example, a rating respective to crispness may be readily correlated with reconstruction parameter values (e.g. filter values) that relate to the tradeoff between sharpness and noise. Thus, if the image recipient rates the image low respective to crispness, the filter may be reduced to increase the sharpness. In this approach, there would optionally be another rating respective to noise or artifacts in order to assess that traded off image aspect.

Where a single overall image quality rating is solicited from the image recipient, this is generally not sufficient to determine which parameter value(s) should be updated. Rather, the single rating is useful in the context of other rated images with which to compare, where those other images employed different reconstruction parameter values. In that context, if the current image used a different value for a certain parameter and the current image is rated lower than previous images, then this is suggestive that the recent change in the parameter value is not preferred by the image recipient. To provide such variation, in some embodiments, probative feedback is provided by employing a feedback test set request sub-module 58 to request automatic generation of one or more test reconstructed images with the value of a selected parameter varied. Typically, the variation of the parameter value is by a certain percentage or preselected amount Δ, e.g. an image with the parameter value increased by 10% and an image with the parameter value decreased by 10%. Such reconstructed images can be generated during dormant cycles of the reconstruction system (typically during the middle of the night). The intended image recipient is then presented with both the image generated using the recipient's profile and also the additional image or images that are generated using that profile but with the selected parameter varied. The recipient chooses (that is, votes for) the best image, and this vote is effectively a vote for the value of the parameter used in generating the elected image (although these details are transparent to the image recipient). To force the image recipient to vote, in some embodiments the request is phrased along the following lines: "Please select which image to use for analysis" and upon selection (i.e., voting) by the image recipient the remaining images are removed from the image workstation 40. Instead of voting for a best image, the image recipient may be requested to rank the images respective to image quality (or an aspect thereof). Such ranking may be more time consuming for the image recipient but does provide additional information for updating the recipient's reconstruction profile.

Another way the feedback acquisition module 54 may acquire feedback is by detecting explicit retrospective reconstructions. Here, the scenario is that the intended image recipient receives the image, finds it unacceptable, and requests a new image reconstruction. Typically, the request will be directed to the technologist or his or her supervisor, and the technologist will "translate" the recipient's objections into (hopefully) improved image reconstruction parameter values, and will repeat the reconstruction using those improved parameter values. The feedback acquisition module 54 detects the repeated reconstruction, identifies the improved parameter values, and updates the image recipient's profile with those values.

Another way the feedback acquisition module 54 may acquire feedback is by monitoring the image recipient's use of post-reconstruction filtering. This approach presupposes that the recipient's image display/review module 36 includes image filtering capability that may be applied to the reconstructed image by the image recipient. The feedback rationale is that the image recipient is likely to perform such filtering only if he or she believes that the filtering may produce a better image, and will make use of the filtered image only if the image recipient does indeed conclude that the filtered image is better than the unfiltered image. If a filtered image is selected for further processing (e.g., image segmentation, cardiac output measurement, or so forth) then the display/review module 36 notifies the feedback acquisition module 54 of this selection. The filter parameter values are also conveyed to the feedback acquisition module 54. Examples of such filtering include (but are not limited to): making the image either sharper or smoother in image space and applying a point spread function in image space. The profile update in this case may entail applying the filter during the image reconstruction (if an equivalent filter is available in the reconstruction module 30) or adjusting other parameter values in a way that "mimics" the filter that was applied by the image recipient. For example, if the image recipient applies an image smoothing filter, then reconstruction parameter values can be adjusted to reduce image sharpness (which increases smoothness), possibly even at the expense of reduced resolution or other objective image degradation.

The profile updating module 56 updates the value or values of one or more parameters of the reconstruction profile of the image recipient. The profile updating module 56 can use techniques in making such an update, depending upon the available feedback information. For example, if the feedback is a vote or ranking of a set of test images, then the update can be as straightforward as selecting the parameter value corresponding to the elected or highest ranked image. Similarly straightforward updating can be performed where the "vote" or implicit, such as when a re-reconstruction is executed using different (and presumably better) parameters, or when the image recipient performs filtering and uses the filtered image in subsequent analysis.

If the feedback is not associated with any specific reconstruction parameter (for example, where the collected feedback is a scalar image rating that rates the overall image and not any particular aspect thereof), then the updating suitably entails determining whether any parameter should be updated and then determining an updated value for any such parameter. For example, if the profile updating module 56 has image ranking values for several comparable images (where "comparable" is suitably assessed, for example, based on the images being of the same anatomical region and using the same image reconstruction algorithm) then the profile updating module 56 suitably determines whether there is any trend in which the variation of a parameter amongst the images correlates with an increasing or decreasing ranking value. If such a correlation is identified, then the trend is suitably extrapolated to estimate a better (not necessarily best) value for the parameter. Optionally, the feedback test set request sub-module 58 may be invoked to request some clarifying test images that use values of the parameter extending into the extrapolation range, and these feedback test images are used in a next iteration to further extend or clarify the optimal value for the parameter.

These last examples assume that the several comparable images use mostly the same reconstruction parameter values, with only one parameter value varied amongst the images. In this case, the profile updating module 56 can suitably operate under the assumption that the single varying parameter is controlling the image recipient's rating or ranking values. If the images have more than one parameter whose value varies amongst the images, then it may be ambiguous as to which parameter is controlling the image recipient's rating values. In one approach, this is addressed by the feedback test set request sub-module 58 being invoked to request some clarifying test images. In another approach, the profile updating module 56 may include an expert system that employs machine learning to simultaneously adjust multiple parameters using a multi-parameter model that suitably incorporates correlations between linked parameters. For example, the model may employ the overall image ranking as the objective function, whose value is computed under the model as a combination of the various image quality aspect metrics. In one approach, each qualitative image quality aspect metric (e.g., crispness, contrast, or so forth) is computed as a term of the objective function that depends upon those reconstruction parameters that are expected to impact that image quality aspect. Parameters that are linked with respect to a particular aspect can be written as a sum of the parameters (possibly individually weighted). Thus, for example, the objective function may be $F_{obj} = w_1 f_{contrast} + w_2 f_{crispness}$ where $f_{contrast}$ is the term pertaining to contrast (and comprises a function of the reconstruction parameters that impact contrast), $f_{crispness}$ is the term pertaining to crispness (and comprises a function of the reconstruction parameters that impact crispness), and $w_1$ and $w_2$ are weights indicative of the expected relative weight that the image recipient is expected to place on contrast and crispness in evaluating the overall image quality. Of course, this simple two-term example is readily expanded to incorporate additional or other terms pertaining to other image quality aspects. The resulting objective function $F_{obj}$ can be optimized respective to the rating assigned to the various available rated images using any suitable machine learning technique.

In any of the parameter value updating performed by the profile updating module 56, various bounds or constraints can optionally be employed. For example, some reconstruction parameters may be fixed such that they cannot be varied from their default settings. These may be manufacturer-controlled settings that are not adjustable by the end-user, or may be otherwise protected settings (for example, set and locked by the imaging laboratory administrator. Typically, such parameters will be omitted from the reconstruction profiles stored in the database 52. When updating an adjustable parameter, constraints may be placed on the update so as to ensure that the updating guided by feedback from the image recipient does not drive the profile into an unacceptable region. For example, it is generally not desirable to allow the feedback-driven profile updating to drive the profile into a region where substantial informational loss is produced. Thus, for example, if the feedback-driven updating continually drives toward a smoother image, this may be constrained to prevent the updating from producing reconstructed images that are so blurry that medically probative features are likely to be washed out entirely. As a further constraint, in some embodiments the setup module 50 displays the set of reconstruction parameter values for review by the technologist prior to performing the reconstruction, and the technologist is able to override any parameter values that he or she finds to be objectionable.

The disclosed reconstruction approaches employing image recipient-specific reconstruction parameter values is described in FIG. 1 as being implemented by the electronic processor 16. In other embodiments, it will be appreciated that these disclosed approaches can be embodied as a non-transitory storage medium storing instructions executable by an electronic processor (such as the illustrative electronic processor 16) to perform the disclosed reconstruction methods. The non-transitory storage medium may, for example, comprise: a hard disk drive or other magnetic storage medium; an optical disk or other optical storage medium; a random access memory (RAM), read-only memory (ROM), flash memory, or other electronic storage medium; or so forth.

Figure 2:
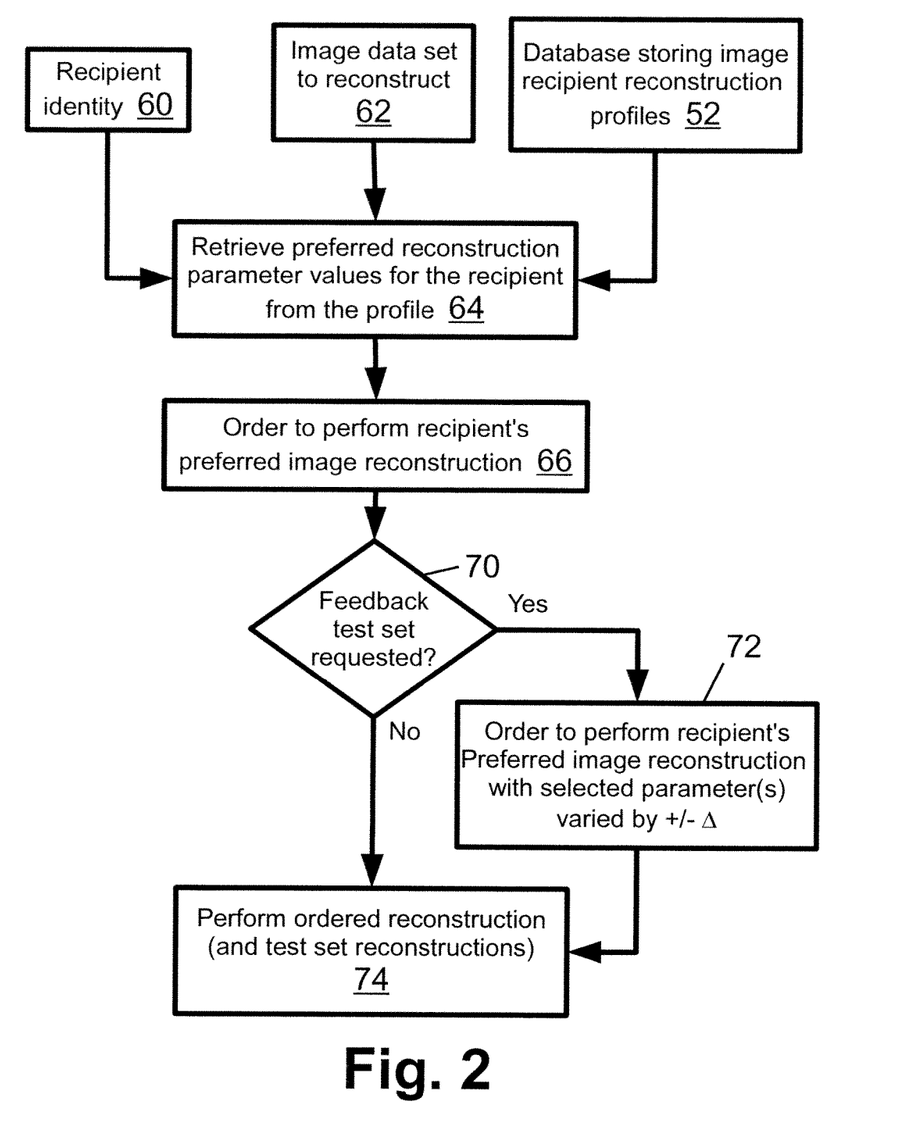
FIG. 2 diagrammatically shows an image reconstruction process suitably performed by the medical imaging facility of FIG. 1.

With continuing reference to FIG. 1 and with further reference to FIG. 2, an example of image reconstruction suitably performed by the modules 30, 50 is shown. The setup module 50 determines the identity 60 of the intended image recipient, and retrieves the imaging data set to reconstruct 62 from the storage 14. In an operation 64, the setup module 50 retrieves the intended image recipient reconstruction profile from the profiles database 52 and constructs an order 66 to perform the recipient's preferred image reconstruction of the imaging data set 62. In a decision operation 70, the setup module 50 determines whether a request for a feedback test set image set has been made by the feedback test set request sub-module 58 of the feedback acquisition module 54. If feedback test image(s) has (or have) been requested, then an additional order 72 is made for each test image. In an operation 74, the image reconstruction module 30 executes the order 66 and, if provided, the additional order(s) 72, in order to generate the reconstructed image for the intended image recipient and (if requested) the one or more test images. The reconstructed image or images are then delivered to the intended image recipient by the delivery module 32 (or, in some alternative embodiments, are manually delivered by mail or courier).

Figure 3:
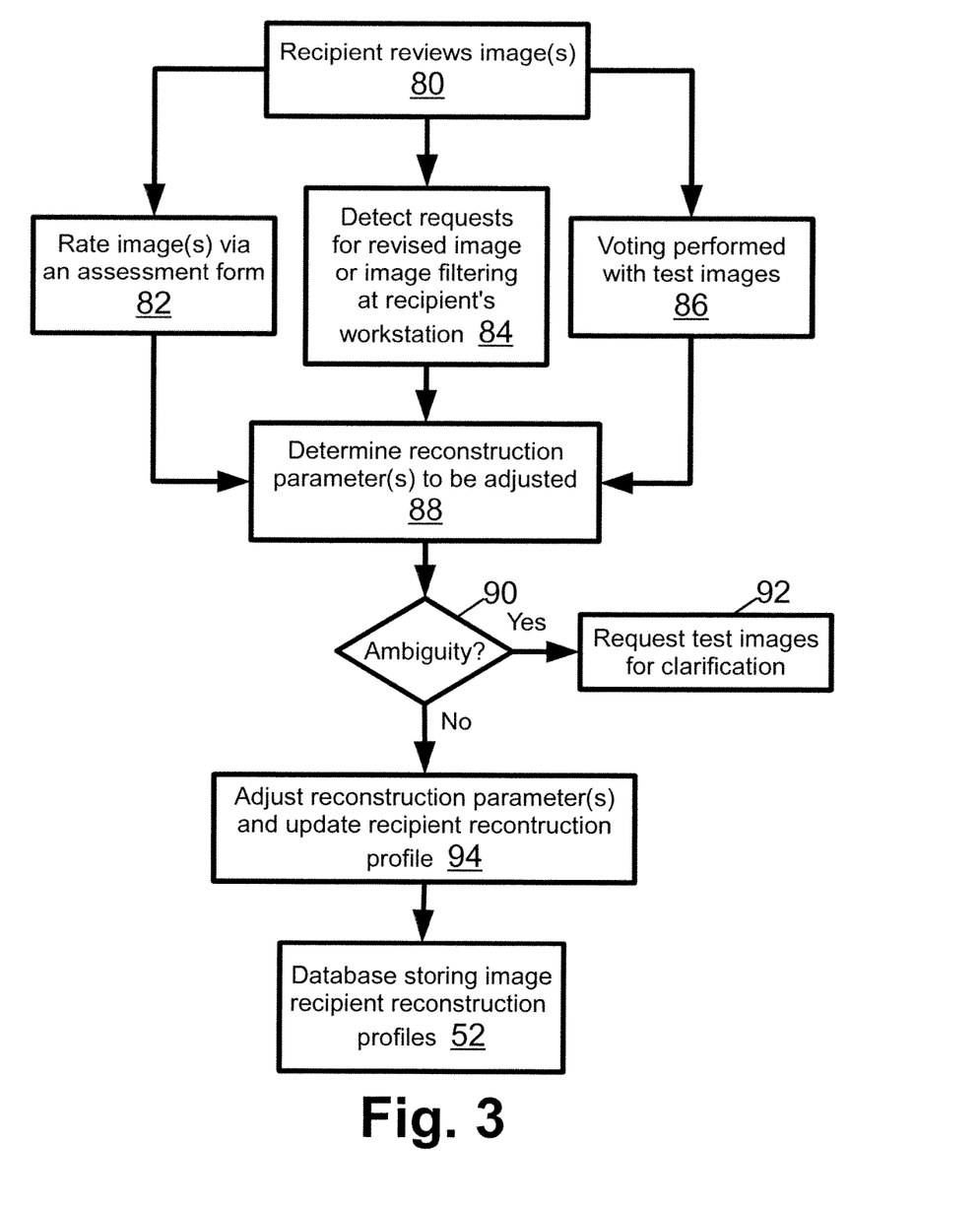
FIG. 3 diagrammatically shows an image review and physician reconstruction profile update process suitably performed by the medical imaging facility and image display workstation of FIG. 1.

With continuing reference to FIG. 1 and with further reference to FIG. 3, an example of a profile update suitably performed by the modules 54, 56 is shown. In a manual operation 80, the intended image recipient reviews the reconstructed image and, if provided, the one or more additional test images. The image recipient provides feedback though one or more available pathways. In the illustrative example of FIG. 3, these available pathways include a feedback operation 82 in which the image recipient rates the images using an assessment form; implicitly provided feedback by requesting a revised image or by performing image filtering at the workstation 40 such request or filtering being detected by the feedback acquisition module 54 in an operation 84; or votes or rankings by the image recipient of a set of images (e.g., including test images) in an operation 86. Based on the feedback, one or more reconstruction parameters are identified for adjustment in an operation 88. In a decision operation 90, if ambiguity is detected in whether or how to update a particular parameter, then the feedback test set request sub-module 58 of the feedback acquisition module 54 is invoked to request test images for clarification in an operation 92. In this case, no update is made and instead the issue of whether/how to update the ambiguous parameter is deferred until the results from the requested feeback test set of images is received. On the other hand, if one or more parameters are unambiguously identified as being ready for updating, then in an operation 94 the value or values of the parameter or parameters is (or are) updated, and the database 52 is updated.

The database 52 that stores image recipient reconstruction profiles (wherein each image recipient reconstruction profile comprises image reconstruction parameter values) should have a format that enables efficient updating and retrieval. In a suitable database configuration, the database 52 contains reconstruction parameters and is indexed (or otherwise organized) by image recipient and reconstruction protocol (encompassing the imaging modality, reconstruction algorithm, and possibly other aspects such as the anatomical region, data acquisition parameters, or so forth), optionally using a composite key. When the results of post-filtering performed by the image recipient at the viewing station 40 are to be applied for subsequent reconstructions, information about the image-space in conjunction with information about the reconstruction (physician, protocol, reconstruction parameters and optionally image acquisition parameters) are sent to the feedback acquisition module 54 where the information is used to update values of reconstruction parameters used for achieving a comparable result in the reconstruction.

The image recipient reconstruction profiles stored in the database 52 can be initialized in various ways. In one approach, all profiles are initialized to the same default set of reconstruction profiles and, thereafter, operation of the updating components 54, 56 serves to gradually adjust the profiles to individual preferences. Optionally, a priori knowledge may be used to initialize a profile in a way more likely to approximate the recipient's preferences. For example, it may be known that imaging systems from a particular manufacturer are designed by default to operate with certain parameter values. If a physician or radiologist newly arrives at the facility (for example, as a new hire) who is used to receiving images from that manufacturer's imaging systems, then that person's profile may suitably be initialized with parameter values comporting with those imaging systems. Similarly, if the radiology facility is upgraded to new imaging systems, one option is to initialize the profiles to values that closely mimic the familiar old imaging system, and to gradually bring in new capabilities via the operation of the updating components 54, 56. In some embodiments, the physician profile is stored on a portable memory device (e.g., a FLASH thumb drive, SIM card, or other portable non-volatile memory device) possessed by the physician, or is accessible at a centralized location (e.g., a physician's profiles database stored at a server computer maintained by the manufacturer and accessible from any imaging facility via the Internet, with suitable password protection or other security). Note that the physician's profile does not contain any patient data, and accordingly does not implicate HIPAA or other patient privacy regulations.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. An apparatus comprising:
a database storing image recipient reconstruction profiles wherein each image recipient reconstruction profile comprises image reconstruction parameter values; and
an electronic processor configured to generate a reconstructed image from medical imaging data by a process including:
retrieving an image recipient reconstruction profile from the database for an intended image recipient,
reconstructing the medical imaging data using iterative forward/backward projection reconstruction or Fourier transform reconstruction with the iterative forward/backward projection reconstruction or Fourier transform reconstruction using image reconstruction parameter values of the retrieved image recipient reconstruction profile to generate the reconstructed image;
controlling a display device to display the reconstructed image; and
performing a profile updating process including:
collecting feedback on the reconstructed image from the intended image recipient wherein the collected feedback is not associated with any specific reconstruction parameter;
updating the image recipient reconstruction profile for the intended image recipient based on the collected feedback, including determining an updated value for a reconstruction parameter based on the collected feedback; and
storing the updated image recipient reconstruction profile in the database.

2. The apparatus of claim 1, wherein the display of the reconstructed image includes at least one feature selected from the group consisting of false color rendering and image filtering.

3. The apparatus of claim 1, wherein the collected feedback is not associated with any specific reconstruction parameter and the updating includes determining an updated value for a reconstruction parameter based on the collected feedback.

4. The apparatus of claim 1, wherein the collected feedback comprises an overall image rating and the updating includes determining an updated value for an image reconstruction parameter based on the overall image rating.

5. The apparatus of claim 1, wherein the electronic processor is configured to perform further operations including reconstructing the medical imaging data using image reconstruction parameter values of the retrieved image recipient reconstruction profile with the value of a selected parameter varied to generate a test reconstructed image, wherein the collected feedback includes a comparison between the reconstructed image and the test reconstructed image, and wherein the updating includes updating the value of the selected parameter based on the comparison.

6. The apparatus of claim 1, wherein:
the collecting of feedback includes re-reconstructing the medical imaging data responsive to a re-reconstruction request received from the intended image recipient wherein the re-reconstructing uses an adjusted parameter value that is different from the value of the parameter in the retrieved image recipient reconstruction profile; and
the updating of the image recipient reconstruction profile includes updating the profile to include the adjusted parameter value.

7. The apparatus of claim 1, wherein the collecting of feedback includes detecting an image filtering operation performed by the intended image recipient on the reconstructed image.

8. A method comprising:
retrieving an image recipient reconstruction profile for an intended image recipient from a database that stores image recipient reconstruction profiles wherein each image recipient reconstruction profile comprises image reconstruction parameter values; and
reconstructing the medical imaging data using iterative forward/backward projection reconstruction or Fourier transform reconstruction with the iterative forward/backward projection reconstruction or Fourier transform reconstruction using image reconstruction parameter values of the retrieved image recipient reconstruction profile to generate the reconstructed image;
collecting feedback on the reconstructed image from the intended image recipient wherein the collected feedback is not associated with any specific reconstruction parameter;
updating the image recipient reconstruction profile for the intended image recipient based on the collected feedback including determining an updated value for a reconstruction parameter based on the collected feedback; and
storing the updated image recipient reconstruction profile for the intended image recipient in the database;
wherein at least the retrieving the reconstructing, the collecting, the updating, and the storing are performed by an electronic processor.

9. The method of claim 8, further comprising:
repeating the reconstructing with the value of a selected reconstruction parameter of the retrieved image recipient reconstruction profile adjusted to generate at least one test image;
wherein the collecting of feedback includes collecting a vote or ranking by the intended image recipient respective to a set of images including the reconstructed image and the at least one test image has the best image quality; and
wherein the adjusting includes adjusting the selected reconstruction parameter based on the vote or ranking.

10. The method of claim 8, wherein:
the collecting of feedback includes re-reconstructing the medical imaging data responsive to a re-reconstruction request received from the intended image recipient wherein the re-reconstructing uses an adjusted parameter value that is different from the value of the parameter in the retrieved image recipient reconstruction profile; and
the updating of the image recipient reconstruction profile includes updating the profile to include the adjusted parameter value.

11. The method of claim 8, wherein:
the collecting comprises detecting an image filtering operation performed by the intended image recipient on the reconstructed image; and
the updating comprises updating the value of a selected image reconstruction parameter of the retrieved image recipient reconstruction profile wherein the selected image reconstruction parameter is selected based on the detected image filtering operation.

12. A non-transitory storage medium storing instructions executable by an electronic processor to perform a method as set forth in claim 8.

13. An apparatus comprising:
a database storing image recipient reconstruction profiles wherein each image recipient reconstruction profile comprises image reconstruction parameter values;
an image reconstruction module configured to reconstruct medical imaging data to generate a reconstructed image; and
an image reconstruction setup module configured to retrieve an image recipient reconstruction profile from the database for an intended image recipient associated with a set of medical imaging data and to invoke the image reconstruction module to reconstruct the set of medical imaging data using projection reconstruction or Fourier transform reconstruction with the projection reconstruction or Fourier transform reconstruction using image reconstruction parameter values of the retrieved image recipient reconstruction profile to generate a reconstructed image for the intended image recipient;
a feedback acquisition module configured to acquire feedback from the intended image recipient pertaining to the reconstructed image for the intended image recipient wherein the collected feedback is not associated with any specific reconstruction parameter; and
a profile updating module configured to update the image recipient reconstruction profile of the intended image recipient based on the acquired feedback including determining an updated value for a reconstruction parameter based on the collected feedback and store the updated image recipient reconstruction profile of the intended image recipient in the database;
wherein the image reconstruction module the image reconstruction setup module, the feedback acquisition module and the profile updating module are implemented by an electronic processor.

14. The apparatus of claim 13, wherein the profile updating module comprises an expert system configured to learn an updated value for at least one parameter of the image recipient reconstruction profile of the intended image recipient.

15. The apparatus of claim 13, wherein the feedback acquisition module comprises:
a feedback test set request sub-module configured to request the image reconstruction setup module generate at least one test reconstructed image by invoking the image reconstruction module to reconstruct the set of medical imaging data using image reconstruction parameter values of the retrieved image recipient reconstruction profile with a selected parameter adjusted away from its value in the retrieved image recipient reconstruction profile;
wherein the feedback acquisition module is configured to acquire a comparative image quality assessment from the intended image recipient comparing the test reconstructed image and the reconstructed image for the intended image recipient; and
wherein the profile updating module is configured to update the image recipient reconstruction profile of the intended image recipient based on the comparative image quality assessment.

16. The apparatus of claim 13, further comprising:
a recipient display and review module implemented by an electronic processor that is the same as or different from the electronic processor implementing the image reconstruction module and the image reconstruction setup module, the recipient display and review module being configured to display the reconstructed image and to perform image filtering on the reconstructed image;
wherein the feedback acquisition module is configured to acquire feedback comprising information pertaining to the image filtering performed by the recipient display and review module from the recipient display and review module.

17. The apparatus of claim 13, wherein each image recipient reconstruction profile comprises image reconstruction parameter values selected from a group consisting of number of iterative reconstruction iterations, pixel or voxel size, relaxation factor, and at least one image filter parameter.

18. A method comprising:
executing image reconstruction operations using an electronic processor wherein each image reconstruction operation retrieves reconstruction parameters specific to an intended image recipient from a database storing image recipient reconstruction profiles and reconstructs imaging data into a reconstructed image for the intended image recipient using Fourier transform reconstruction with the Fourier transform reconstruction using the reconstruction parameters specific to the intended image recipient retrieved from the database;
updating the reconstruction parameters specific to respective intended image recipients based on feedback on the reconstructed images received from the respective intended image recipients wherein the collected feedback is not associated with any specific reconstruction parameter, and wherein the updating is performed by the electronic processor, the updating of reconstruction parameters specific to an intended image recipient being based on feedback from the intended image recipient comprising an image quality comparison between two or more reconstructed images for the intended image recipient;
storing the updated reconstruction parameters specific to respective intended image recipients in the database storing image recipient reconstruction profiles; and
displaying or printing reconstructed images for the intended image recipients.

19. The method of claim 18, wherein the updating comprises:
performing machine learning to adjust a set of reconstruction parameters using a multi-parameter model incorporating correlations between linked parameters of the set of reconstruction parameters.

20. The method of claim 18, further comprising:
transferring an image recipient reconstruction profile comprising the reconstruction parameters specific to the intended image recipient from a portable non-volatile memory device to the database storing image recipient reconstruction profiles.

* * * * *